United States Patent [19]

Ivaschenko et al.

[11] Patent Number: 4,457,859
[45] Date of Patent: Jul. 3, 1984

[54] MESOMORPHIC MATERIAL CONTAINING 2,2'-AZOIMIDAZOLE COMPOUNDS CONTAINING 1,1'-BENZYLIDENEAMINO SUBSTITUENTS

[76] Inventors: Alexandr V. Ivaschenko, Pervomaiskaya, 44a, kv. 57; Valentina T. Lazareva, Oktyabeskaya, 22, Korpus 3, kv. 19; Elena K. Prndnikova, Likhachevskoe shosse, 20, kv. 29; Vladimir G. Rumyantsev, Likhachevskoe shosse, 20, Korpus 1, kv. 165; Tamara S. Pliusnina, Likhachevskoe shosse, 20, kv. 22, all of Dolgoprudny Moskovskoi oblast; Viktoe A. Nefedov, pereylok Obukha, 4, kv. 62, Moscow; Lev M. Blinov, ulitsa Dubninskaya 2, Korpus 5, kv. 79, Moscow; Viktor V. Titov, ulitsa Festivalnaya, 12, kv. 95, Moscow; Vladimir P. Sevostyanov, ulitsa B. Khmelnitskogo, 20/24, kv. 25, Saratov, and Vadim M. Shoshin, ulitsa Polevaya, 7, kv. 69, Fryazino Moskovskoi oblastia, all of U.S.S.R.

[21] Appl. No.: 364,848
[22] PCT Filed: Jun. 25, 1981
[86] PCT No.: PCT/SU81/00059
§ 371 Date: Mar. 23, 1982
§ 102(e) Date: Mar. 23, 1982
[87] PCT Pub. No.: WO82/00472
PCT Pub. Date: Feb. 18, 1982

[30] Foreign Application Priority Data

| Jul. 31, 1980 [SU] | U.S.S.R. | 2967265 |
| Jul. 31, 1980 [SU] | U.S.S.R. | 2967803 |
| Jul. 31, 1980 [SU] | U.S.S.R. | 2967844 |
| Jul. 31, 1980 [SU] | U.S.S.R. | 2967311 |

[51] Int. Cl.³ .................. C07D 233/88; C09K 3/34; C08L 63/00
[52] U.S. Cl. .................. 252/299.61; 252/299.1; 252/299.68; 260/157; 548/337; 564/237; 568/325; 568/335
[58] Field of Search .......... 252/299.1, 299.61, 299.68; 260/157

[56] References Cited

U.S. PATENT DOCUMENTS

3,646,040 2/1972 Horstmann et al. .............. 260/152

FOREIGN PATENT DOCUMENTS

564813 11/1973 Fed. Rep. of Germany ... 252/299.1

OTHER PUBLICATIONS

Chemische Berichte Herausgegeben Von, with translation, Der Gesellschaft Deutscher Chemiker, 101 Jahrgang, Heft 9/1968, SS. 3151–3162, with translation, (Beyer et al.).

L. M. Blinov–Electro–and Magnetooptics of Liquid Crystals, (Moscow, "Nauka", Publishers, Chief Editorial Board for Physico–Mathematical Literature, 1978, pp. 148–152), with translation.

*Primary Examiner*—Floyd D. Higel
*Attorney, Agent, or Firm*—Robert E. Burns; Emmanuel J. Lobato; Bruce L. Adams

[57] ABSTRACT

2,2-azimidazole derivatives of the formula:

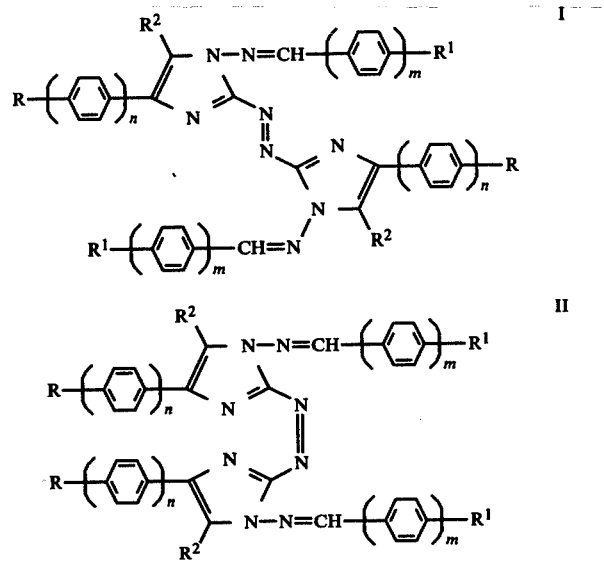

wherein R and $R^1$ are H, a $C_1$–$C_{12}$ alkyl, a $C_1$–$C_{12}$ alkoxy; $NO_2$; $R^2$ is hydrogen, a $C_1$–$C_3$ alkyl; n, m=1 to 3, but where n—m=1, $R=R^1=R^2=H$ is excluded, are disclosed as well as a method for preparing these compounds by oxidation of a compound of the formula

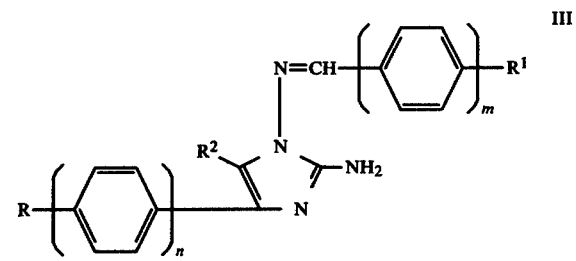

wherein R, $R^1$, $R^2$, n and m are as identified above, except for the compound, wherein $R=R^2=R^2=H$, n=m=1. A liquid-crystal or mesomorphic material containing the 2,2'-azoimidazole compounds and electrooptical device comprised of such mesomorphic material are disclosed. The electrooptical devices are useful for systems of electronic representation and processing of information. The compounds therein have two spectrally spaced absorption bands in the visible part of their spectrum such that their position insures the contrast required for the human eye to be able to readily recognize the difference in color.

10 Claims, No Drawings

MESOMORPHIC MATERIAL CONTAINING 2,2'-AZOIMIDAZOLE COMPOUNDS CONTAINING 1,1'-BENZYLIDENEAMINO SUBSTITUENTS

FIELD OF THE INVENTION

The present invention relates to novel dichroic dyestuffs for liquid crystals and, more specifically, to 2,2'-azoimidazole derivatives, a method for preparing same, a mesomorphic material and an electrooptical device.

BACKGROUND OF THE INVENTION

Among 2,2'-azoimidazole derivatives currently known is 1,1'-bisbenzylideneamino-4.4'-diphenyl-2,2'-azoimidazole described in FRG Journal (Chem.Ber., vol.101, September 1968, Verlag Chemie, Valgheim, Beyer A., Hetzheim, H. Honeck, D. Linq, T. Pyl "Synthesis of Novel Imidazole Derivatives", p.3151–3162).

However, a utility of the above-mentioned compound has not been described anywhere.

A great number of dyestuffs are known in the art for mesomorphic materials featuring a positive dichroism (cf. U.S. Pat. No. 3,703,329 published 21.11.1972, Cl. 350-150). At a planar orientation of the mesomorphic material, e.g. with a positive anisotropy, incorporating a dyestuff with positive dichroism (S above O) the working field in a electrooptical device looks coloured. If a voltage applied to the electrooptical device is above some critical value, the orientation of the mesomorphic material becomes homeotropic and the working field looks faintly coloured. Dyestuffs with a negative dichroism under the above-specified conditions give a reverse picture and a combination of dyestuffs with positive and negative dichroism makes it possible to obtain colour shifting in the electrooptical device, provided that these dyestuffs have spectrally spaced absorption bands within the visible region of spectrum.

While as it has been mentioned hereinbefore, dyestuffs with a positive dichroism are known in a sufficiently broad range, dyestuffs with a negative dichroism which are of a practical interest are limited to tetrazine derivatives (cf.French Pat. Nos. 2,416,253; 2,422,707; 2,428,666 Cl. C 09 K 3/34, published 1978, 1978 and 1979 respectively).

Among the dyestuffs for mesomorphic materials having two absorption bands in the visible region of the spectrum with dichroism of opposite signs, only bis-merocyanine is known which has an absorption band with the maximum at 574 nm (S above O) and an absorption band with the maximum at 482 nm (S below O) (cf. Doklady Akademii Nauk SSSR, vol. 220. February 1975, "Nauka" Publishing House, Moscow: L. M. Blinov, G. G. Dyadyusha, F. A. Mikhailenko, I. L. Mushkalo, V. G. Rumyantsev "Polarization of absorption bands of Solutions of Biscyanine Dyes in Liquid Crystals", pp. 860–862). However, this dyestuff has, on the one hand, absorption bands located in the visible area of spectrum such that their position does not ensure the contrast required for a human eye. Furthermore, this dyestuff makes it possible to obtain, in an electrooptical device, light signs against a dark background which is also unsatisfactory for perception by a human eye.

Dyestuffs for mesomorphic materials having two spectrally spaced absorption bands within the visible area of spectrum, so that the long-wave band has a negative dichroism and the short-wave band has a positive dichroism, are not known at all.

Due to the lack of dichroic dyestuffs of the latter type there is also lack of appropriate mesomorphic materials and corresponding electrooptical devices.

DISCLOSURE OF THE INVENTION

The present invention is directed to the provision of novel 2,2'-azoimidazole derivatives having two spectrally spaced absorption bands in the visible part of their spectrum wherein the long-wave band has a negative dichroism in a mesomorphic material and the short-wave band—a positive dichroism; the invention is also directed to the provision of a method for preparing these 2,2'-azoimidazole derivatives and, creation, on their basis, of a mesomorphic material or liquid crystal and an electrooptical device.

This object is accomplished by our discovery of trans-and cis-2,2'-azoimidazole derivatives which, according to the present invention correspond to the general formula I or II:

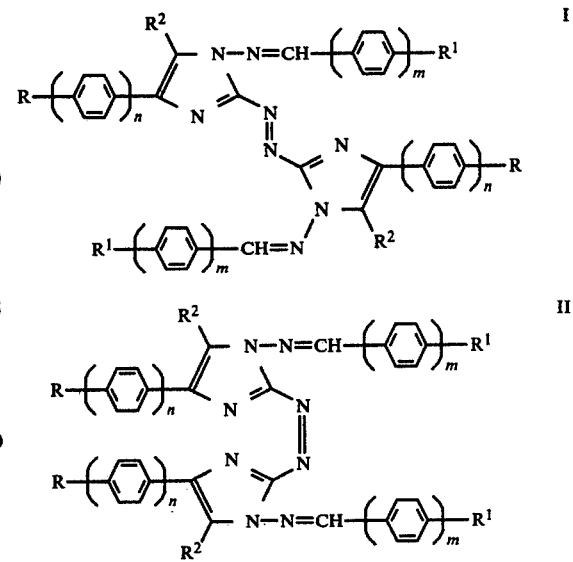

wherein R and R' are the same or different and each represents hydrogen, an alkyl or an alkoxy containing each 1 to 12 carbon atoms or $NO_2$; $R^2$ is hydrogen or an alkyl containing to 3 carbon atoms; n and m are the same or different and each represents an integer of from 1 to 3 so that where $n=m=1$; the compound wherein $R=R'=R^2=H$ is excluded.

2,2'-Azoimidazole derivative of the general formulae I and II have two spectrally spaced absorption bands in the visible spectrum area so that the long-wave band has a negative dichroism and the short-wave-a positive one. The structure of the novel compounds of the general formulae I and II is justified by the data of elemental analysis, electron spectra and dichroism or absorption bands measured in a mesomorphic matrix. In electron spectra of trans-2, 2'-azoimidazoles of the general formula (I), as it could have been expected, the long-wave absorption bands are biased bathochromically as compared to corresponding bands in electron spectra of cis-2,2'-azoimidazoles of the general formula II.

According to the present invention, 2,2'-azoimidazole derivatives of general formulae I and II are prepared by way of oxidation of an imidazole of the general formula III:

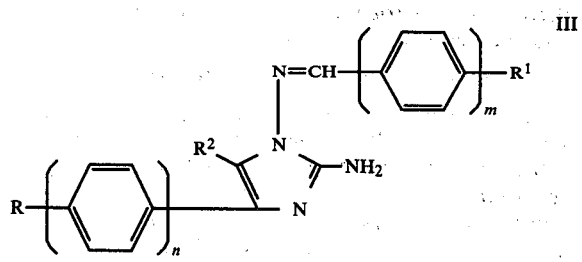

wherein R, $R^1$, $R^2$, n and m are as identified hereinbefore, with the exception of a compound, wherein $R=R'=R^2=H$, $n=m=1$, by means of manganese dioxide in an aromatic hydrocarbon upon heating, followed by isolation of the described product; or the above specified derivatives of 2,2'-azoimidazole are prepared by reacting aminoguanidine hydrazones of the general formula IV:

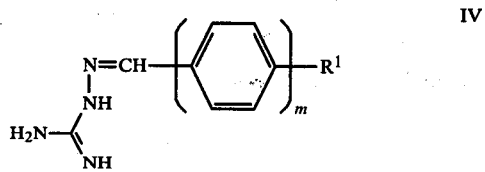

wherein $R^1$ and m are as identified hereinbefore, with α-bromoketone of the general formula V:

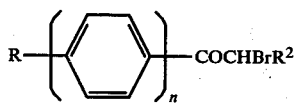

wherein R, $R^2$ and n are as identified hereinbefore, with the proviso that if in a compound IV $R'=H$, $m=1$, a compound V, wherein $R=R^2=H$ and $n=1$ is excluded, in a lower alcohol upon heating in the presence of air, followed by isolation of the desired product.

It is also an object of the present invention to provide a mesomorphic material or liquid crystal which makes it possible to change colours in an electrooptical, which, according to the present invention comprises 0.4–3.5% by weight of at least one 2,2'-azoimidazole derivatives of the general formula I or II or a mixture of both, wherein R and $R^1$ are the same or different and each represent hydrogen, a $C_1$-$C_{12}$ alkyl, a $C_1$-$C_{12}$ alkoxy, $NO_2$; $R^2$ is hydrogen, a $C_1$-$C_3$ alkyl; n and m are each an integer of from 1 to 3, and a mesomorphic matrix in an amount sufficient to ensure the balance (up to 100% by weight). The compounds corresponding to formula I or II, wherein $R=R^1=R^2=H$ and $m=n=1$, though being known, as it has been mentioned hereinbefore, have not been used previously as a component for a mesomorphic material, as is now suggested for this material.

The above-mentioned mesomorphic material can also contain 0.3 to 3.0% by weight of a dyestuff possessing a positive dichroism.

According to the present invention, it is advisable to use, as the dyestuff with a positive dichroism, a blue or green dyestuff with a positive dichroism.

The mesomorphic material according to the present invention has two absorption bands in the visible part of spectrum and the long-wave band has a negative, and the short-wave band—a positive dichroism.

If a mesomorphic material contains the above-mentioned dyestuff with a positive dichroism, in this case it has three absorption bands in the visible part of spectrum so that the long-wave and short-wave bands have a positive dichroism, while the medium-wave band has a negative dichroism. The material according to the present invention reveals either a common effect or a cholesteric effect of the "guest-host" type and enables colour switching-over in an electrooptical device.

It is a further object of the present invention to provide an electrooptical device enabling switching-over colours which according to the present invention has a dichroic working body comprising a layer of the above-specified mesomorphic material positioned between transparent electrodes provided with a source of voltage control; this working body has two absorption bands within the visible part of spectrum so that the long-wave band manifests a negative dichroism and the short-wave band—a positive one. In the case where the mesomorphic material contains a working body incorporating, a dyestuff with a positive dichroism, the working body has three absorption bands in the visible part of spectrum so that the long-wave and short-wave bands have a positive dichroism, while the medium-wave band has a negative dichroism.

The electrooptical device according to in invention is useful for the presentation and processing of information.

BEST MODE FOR CARRYING-OUT THE INVENTION

The present invention is concerned mainly with the provision of novel 2,2'-azoimidazole derivatives corresponding to general formulae I and II.

The compound demonstrating the best spectral characteristics is a compound of the general formula I, wherein R H—$C_8H_{17}$, $R^1=R^2=H$, $n=2$, $m=1$ and and which has two absorption bands in the visible part of the spectrum with their maximum at 430 and 550 nm and which reveal positive and negative dichroism respectively: $S_{430}=0.64$; $S_{550}=0.58$.

The 2,2'-azoimidazole derivatives according to the present invention corresponding to formula I or II should be produced by reacting an appropriate solution of 2-amino-1-arylideneaminoimidazole of formula III in an aromatic hydrocarbon with manganese dioxide upon heating with azeotropic distillation of water formed in the reaction for 2 to 4 hours, followed by filtration of the reaction mass to remove manganese salts and cooling the thus obtained solution, with a subsequent isolation of the desired product by conventional techniques. This method is the most convenient in practicing of the present invention.

In accordance with the present invention use can be made of any derivatives of 2-amino-1-arylideneaminoimidazoles the general formula III, except for the compound, wherein $R=R^1=R^2=H$, and $n=m=1$. The most preferred are compounds, wherein R and $R^1$ are n-alkyl or n-alkoxy radicals containing 1 to 12 carbon atoms, $R^2$ is hydrogen and $n=2$ or 3, $m=1$.

The desired products prepared according to the present invention can be isolated from the reaction mass by any methods known in the organic chemistry such as evaporation of the reaction solution resulting from separation of manganese salts, recrystallization of the residue or chromatographic treatment of the above-mentioned solution, or by any other methods.

The best embodiment of the present invention relative to the mesomorphic material consists in that this mesomorphic material is composed of 1% of a compound of formula I, wherein R=H—$C_8H_{17}$, $R^1=R^2=H$, n=2, m=1, and 99% of a mesomorphic matrix. The mesomorphic matrix should preferably have a positive dielectric anisotropy and maximum possible temperature range of the nematic mesophase, room temperature inclusive. This material makes it possible to obtain, in electrooptical systems for presentation and processing of information based on the use of the "guest-host" effect violet signs against a light-brown background with a high contrast of the image on the whole.

The mesomorphic material according to the present invention comprises a mesomorphic matrix consisting of one or more mesomorphic compounds. In the latter case mesomorphic substances may pertain to both the same homologous series of substances and to different homologous series and classes of substances such as azoxybenzene derivatives, diphenyl derivatives, phenylbenzoate derivatives, Schiff's bases and the like.

According to the present invention, the electrooptical device comprises a dichroic working body composed of a layer of a mesomorphic material incorporating a compound of the general formula I, wherein R is H—$C_8H_{17}$, $R^1=R^2=H$, n=2, m=1 and 99% by weight of a mesomorphic matrix interposed between transparent electrodes provided with a source of voltage control. This device is successfully useful in various electrooptical and optoelectronic systems for information presentation and processing, for example in electronic watch, computers, different information displays, light valves, advertizing tableaux and the like.

The present invention is further explained by the following illustrative examples.

The novel compounds—trans- and cis-2,2'-azoimidazole derivatives are shown in Table 1 which also represents their elemental analysis data and electron spectra supporting the structure of the compounds.

The methods for preparing these compounds are illustrated by Examples 1 to 6, Examples 7 to 14 illustrate the mesomorphic material according to the present invention and Examples 15 to 20 illustate the electrooptical device.

EXAMPLE 1

To a solution of 97.4 g of n-heptylbenzeneacetophenol in 100 ml of acetic acid, there are added under stirring for 1.5 hour, 23 ml of bromine (at a temperature within the range of from 20° to 40° C.). The reaction mass is kept for one hour at a temperature of from 20° to 25° C. and poured into water. The organic layer is extracted with chloroform. The extract is washed with a 5% aqueous soda solution, water and dried with sodium sulphate. The solution is decanted, chloroform is distilled-off in vacuum. There are thus obtained 127.6 g of ω-bromo-4-heptylacetophenone which is used in the next stage and further Examples without any additional purification. 29.7 g of the resulting ω-bromo-4-heptylacetophenone and 32.4 g of benzaldehydeguanylhydrazone are refluxed for 5 hours in 300 ml of ethanol. The hot reaction mass is filtered, the filter cake is washed with 100 ml of boiling ethanol, dried and recrystallized from a minimal amount of acetic anhydride. There is obtained 0.5 g of 1,1'-bisbenzylideneamino-4,4'-di(4-heptyl-phenylene)-2,2'-azoimidazole [II/I/]. The electron spectrum and data of elemental analysis are shown in Table 1 hereinbelow. In Table 1 and other Tables given hereinafter the compounds of formulae 1 and II for purposes of succinctness are denoted by two figures, the former indicating the relation of the compound to formulae (I and II), the second figure in brackets points to the Example illustrating the preparation of this compound.

EXAMPLE 2

To a solution of 55.3 g of aminoguanidine hydrochloride in 125 ml of water there is added n-ethoxybenzaldehyde in the amount of 75.1 g. The reaction mass is heated to the temperature of 80° C. and maintained at this temperature for 10 minutes, whereafter it is cooled to 60° C. and combined, under stirring, with a solution of 22 g of caustic soda in 75 ml of water. Then the reaction mass is cooled to room temperature, the residue is filtered-off, washed with 50 ml of cold water and dried. There are obtained 99 g of n-ethoxybenzaldehydeguanylhydrazone which is used in the subsequent stage and further Examples without any additional purification. 29.7 g of ω-bromo-4-heptylacetophenone (prepared as in Example 1) and 37.4 g of n-ethoxybenzaldehydeguanylhydrazone are reacted following the procedure described in the foregoing Example 1. There is obtained 0.7 g of 1,1'-bis-(n-ethoxybenzylideneamino)-4,4'-di-(4-heptylphenylene)-2,2'-azoimidazole (II /2/). The data of analysis are shown in Table 1.

EXAMPLE 3

To a solution of 30.9 g of 4-acetyl-4'-octylbiphenyl in 50 ml of acetic acid there are added 5.1 ml of bromine for one hour under stirring at the temperature of 50° C. The reaction mass is stirred for 1 hour at room temperature, poured into water, the organic layer is extracted with chloroform, the extract is washed with a 5% aqueous solution of soda, then with water and dried with sodium sulphate. Chloroform is distilled-off in vacuum and the residue is recrystallized from a minimum amount of ethanol to give 38 g of 4-bromoacetyl-4'-octylbiphenyl; from 19.6 g of the product and 16.5 g of benzaldehydeguanylhydrazone there is obtained, following the procedure of Example 1, 0.65 g of 1,1'-bis-benzylideneamino-4,4'-di-[4-(4-octylphenylene)-phenylene]-2,2'-azoimidazole (II /3/). The analysis data are shown in Table 1 hereinbelow.

EXAMPLE 4

The synthesis is conducted as described in Example 1 hereinbefore. From 19.6 g of 4-bromoacetyl-4-octyl-biphenyl and 18.7 g of 4-ethoxybenzaldehydeguanylhydrazone there is obtained 0.7 g of 1,1'-bis-(4-ethoxybenzylideneamino)-4,4'-di-[(4-octylphenylene)-phenylene]-2,2'-azoimidazole/mixture of I (4) and II (4)/. The analytical data are shown in Table 1.

EXAMPLE 5

The synthesis is conducted following the procedure described in Example 2. From 75.5 g of 4-nitrobenzaldehyde and 55.3 g of aminoguanidine hydrochloride there are obtained 102.3 g of 3-nitrobenzaldehydeguanylhydrazone. From 37.5 g of the latter and and 29.7 g of ω-bromo-4-heptylacetophenone, as described in Example 1, there is obtained 0.07 g of 1,1'-bis-(4-nitrobenzylideneamino)-4,4'-di-(n-heptylphenylene)-2,2'- azoimidazole (II /5/). The data of corresponding analysis are given in Table 1.

EXAMPLE 6

31.9 g of 2-amino-1-benzylideneamino-4-(4-n-octyl-4'-biphenylene)-imidazole and 49.8 g of $MnO_2$ are heated at reflux with azeotropic ditillingoff water in toluene (2 liters) for 3-4-hours. The reaction mass is filtered. The filtrate is evaporated to the volume of 0.6 l and then cooled. The residue is filtered-off and recrystallized from benzene. There are prepared 1.9 g of a compound which is dissolved in a minimum volume of chloroform and subjected to chromatography on alumina. As the eluent use is made of a mixture benzene-acetone in the ratio of 10:1. There are obtained 1.8 g of trans-2,2'-azoimidazole of formula (I), wherein R is $C_8H_{17}$, n=2, R'=H, m=1, $R^2$=H, and 0.1 g of cis-2,2'-azoimidazole of formula (II), wherein R is $C_8H_{17}$, n=2, R'=H, m=1, $R^2$=H.

EXAMPLES 7 THROUGH 14

A specified amount of a dyestuff with a positive dichroism and/or 2,2'-azoimidazole derivative of formula I and/or II is dissolved in a mesomorphic matrix. The resulting mesomorphic material is ready for use. Table 3 shows compositions of the mesomorphic material and colour switching over. In addition to the notions assumed in Examples 1 to 6, in Table 3 the following indications of the components are used:

DK-1—5-hydroxy-2-naphthol-2'-indolylindigo $\lambda_{max}$=625 nm, S= +0.63)—blue dyestuff;

DK-2 —1-methylamino-4-(4'-azo-4"methoxyphenyl)-aminoanthraquinone, $\lambda_{max}$=450 and 620 nm, $S_{450}$=0.42 and $S_{629}$=0.51—green dyestuff;

DK-3 13 2,2'-azoimidazole of formula (II), wherein R=R'=$R^2$=H, n=m=1 ($\lambda_{max}$=390 and 530 nm, $S_{390}$= +0.5 and $S_{530}$= −0.28);

GK-1—mesomorphic matrix consisting of n-cyanophenyl esters of aromatic acids ($\Delta\epsilon$= +19);

GK-2—mesomorphic matrix consisting of azoxybenzenes and n-cyanophenyl esters of aromatic acids ($\Delta\epsilon$= +3.5);

GK-3—mesomorphic matrix consisting of n-cyanodiphenyls ($\Delta\epsilon$= +13).

The data of elemental analysis and electron spectra of 2,2'-azoimidazole derivatives of the general formula I and II are shown in Table 1 hereinbelow.

in an oriented mesomorphic matrix consisting of n-cyanophenyl esters of n-alkylbenzoic and n-alkylcinnamic acids.

TABLE 2

| Dyestuff of Example | $\lambda_{max}$, nm | $S_{\lambda max}$ |
|---|---|---|
| II(I) | 400 | 0.57 |
| Example 1 | 530 | −0.48 |
| II(2) | 430 | 0.50 |
| Example 2 | 540 | −0.26 |
| I(3) | 430 | 0.64 |
| Example | 550 | −0.58 |
| II(3) | 395 | 0.56 |
| Example 3 | 530 | −0.58 |
| I(4) | 440 | 0.66 |
| Example 4 | 560 | −0.42 |
| II(5) | 400 | 0.47 |
| Example 5 | 550 | −0.30 |
| I(6) | 430 | 0.64 |
| Example 6 | 550 | −0.58 |

TABLE 3

| No. | Component and its content (wt. %) | Colour switching-over upon the material transition from planar to homeotropic state |
|---|---|---|
| 1. | 0.7% II (1) 99.3% GK-1 | yellow-crimson |
| 2. | 0.7% DK-3 99.3% GK-1 | yellow-orange-crimson |
| 3. | 0.4% I(4) 99.6% GK-1 | yellow-violet |
| 4. | 0.7% I(3) 99.3% GK-1 | yellow-violet |
| 5. | 1.5% II(2) 98.5% GK-1 | yellow-violet |
| 6. | 0.9 DK-1 0.7 DK-3 98.4 GK-1 | blue-crimson |
| 7. | 0.3% DK-2 0.7% DK-3 99.0% GK-1 | green-crimson |
| 8. | 1.6% DK-1 0.7% DK-3 97.7% GK-2 | green-violet-crimson |
| 9. | 1.6% DK-1 0.7% DK-3 97.7% GK-3 | green-violet-crimson |
| 10. | 1.2% DK-1 0.7% II(1) 98.1% GK-1 | blue-green-crimson |
| 11. | 0.7% II(I) 12% cholesteryl chloride 87.3% GK-3 | yellow-crimson |
| 12. | 0.7% DK-3 12% cholesteryl chloride 87.3% GK-1 | yellow-orange-crimson |

TABLE 1

| Compound of Example | M.p. °C. | Found, % C | H | N | Gross formula | Calculated, % C | H | N | Electron spectrum in ethanol λ max (lgE) |
|---|---|---|---|---|---|---|---|---|---|
| II(I) | 184.2–186 | 76.74 | 7.07 | 15.68 | $C_{46}H_{52}$ $N_8$ | 77.05 | 7.32 | 15.63 | 281(4.57), 385(4.42), 526(4.13) |
| II(2) | 194.9–196.1 | 74.25 | 6.90 | 13.89 | $C_{50}H_{60}$ $N_8O_2$ | 74.59 | 7.51 | 13.92 | 292(4.53), 345(4.37), 417(4.25), 532(4.09) |
| II(3) | 232–233.5 | 79.82 | 7.01 | 12.31 | $C_{60}H_{64}$ $N_8$ | 80.32 | 7.19 | 12.49 | $278^x$(4.50), 307(4.57) 417(4.45), 533(4.05) |
| mixture I(4)+ +II(4) | 204–206 | 78.78 | 7.11 | 11.49 | $C_{64}H_{72}$ $N_8O_2$ | 78.03 | 7.36 | 11.37 | $278^x$(4.54), 310(4.63) 375(4.46), 543(4.47) |
| II(5) | 214 | 68.12 | 6.35 | 17.20 | $C_{46}H_{50}$ $N_{10}O_4$ | 68.46 | 6.26 | 17.35 | 286(4.55), 394(4.25), 533(4.10) |
| I(6) | 213–215 | 80.12 | 7.09 | 12.30 | $C_{60}H_{64}$ $N_8$ | 80.32 | 7.19 | 12.49 | 263(4.37), 395(4.18), 526(3.80), 289(4.37), 512(3.82) |

$^x$- shoulder.

Table 2 shows the data on dichroism of longwave absorption bands of novel derivatives of 2,2'-azoimidazole of the general formulae I and II measured TABLE 3-continued

| No. | Component and its content (wt. %) | Colour switching-over upon the material transition from planar to homeotropic state |
|---|---|---|
| 13. | 0.7% I(3) 12% cholesteryl chloride 87.3% GK-1 | yellow-violet |
| 14. | 1% II(I) 0.4% DK-2 12% cholesteryl chloride 86.6% GK-3 | green-crimson |

EXAMPLES 15 AND 16

Use is made of a working body interposed between electrodes and containing 99% by weight of a liquid crystal GK-1 with positive dielectric anisotropy and 1% by weight of a dyestuff II(I) or II(6) having two absorption bands with a width of 100–140 nm and maximum near 390–400 nm and 530 nm within the visible range of spectrum; the former out of the above-mentioned bands has a positive dichroism, the latter—negative one.

The starting orientation of the working body with the width of 20 μm in planar or twisted to 90° ("twist"-structure), and its colour for polarized light is yellow or yellowish-orange. Applied to the electrodes is an electric field with the frequency of 20 Hz and intensity of 5×10 V/cm. A homeotropic structure with a crimson colour is obtained.

EXAMPLES 17 TO 19

Similar results are obtained in the case of a device with a working body consisting of 99.3% of GK-1 and 0.7% of a dyestuff II (2) or I (4), or I(3) having its shortwave absorption band with the maximum near 430–440 nm featuring a positive dichroism, while the absorption band with the maximum near 540–560 nm has a negative dichroism. The width of these bands is 100–140 nm. A colour switching-over from yellow to violet is obtained. Table 4 shows embodiments of a working body, wavelengths of their absorption maximum in the visible part of spectrum, the degree of regularity of corresponding absorption oscillators and the observed colour switching-over.

EXAMPLE 20

Use is made of a working body consisting of 0.7% by weight of DK-3, 12% by weight of cholesteric liquid crystal of cholesteryl chloride and 87.3% by weight of a liquid crystal with a posititive dielectric anisotropy GK-3. The starting texture of the working body having thickness of 20 μm is planar and of yellow colour. The electric field with the frequency of 200 Hz is applied to the electrodes, the field intensity being $10^4$ V/cm. A homeotropic structure of a crimson colour is obtained. The colour switching-over in this case is observed without a polaroid.

TABLE 4

| Dyestuff | Wavelength of absorption maximum, nm | Degree of absorption regularity | Observed colour switching-over |
|---|---|---|---|
| II(6) | 400 | 0.57 | yellow-crimson |
|  | 530 | −0.24 |  |
| II(1) | 390 | 0.5 | yellowish-orange-crimson |
|  | 530 | −0.14 |  |
| II(2) | 440 | 0.66 | yellow-violet |
|  | 560 | −0.21 |  |
| I(4) | 530 | 0.64 | yellow-violet |
|  | 550 | −0.29 |  |
| I(3) | 430 | 0.5 | yellow-violet |

TABLE 4-continued

| Dyestuff | Wavelength of absorption maximum, nm | Degree of Observed colour regularity switching-over |
|---|---|---|
|  | 540 | −0.13 |

Industrial Applicability

The novel 2,2'-azoimidazole derivatives of the general formulae I and II according to the present invention is useful in the manufacture of mesomorphic materials to be used in electrooptical devices for information presentation and processing widely employed in electronics.

We claim:

1. A mesomorphic material, comprising 0.4 to 3.5% by weight of at least one as cis- or trans-2,2'-azoimidazole or a mixture thereof of the formula:

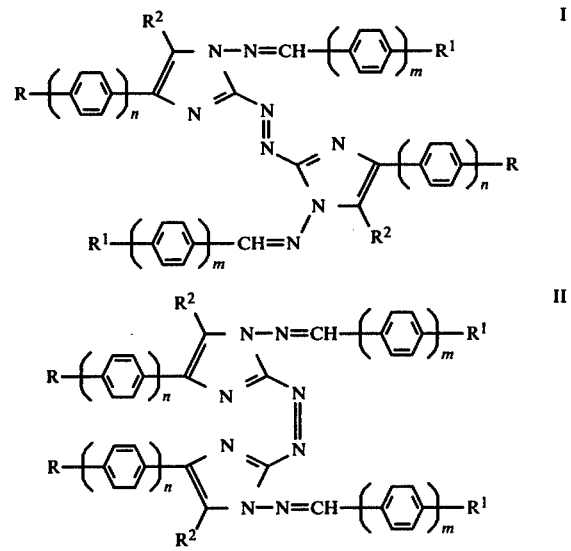

wherein R and $R^1$ are the same or different and each represents hydrogen, an alkyl or an alkoxy containing 1 to 12 carbon atoms or $NO_2$; $R^2$ is hydrogen or an alkyl containing 1 to 3 carbon atoms; n and m are the same or different and each represents an integer of from 1 to 3, and up to 100% by weight of a mesomorphic matrix.

2. The mesomorphic material according to claim 1, which further contains 0.3 to 3.0% by weight of a dyestuff with a positive dichroism.

3. The mesomorphic material of claim 4 wherein the dyestuff is blue or green.

4. The mesomorphic material of claims 1 or 2 wherein said 2,2'-azoimidazole is the trans-form.

5. The mesomorphic material of claims 1 or 2 wherein said 2,2'-azoimidazole is the cis-form.

6. The mesomorphic material of claims 1 or 2 wherein said 2,2'-azoimidazole is a compound in which R and $R^1$ are each n-alkyl or n-alkoxy groups containing 1 to 12 carbon atoms, $R^2$ is hydrogen, n=2 or 3 and m=1.

7. The mesomorphic material of claims 1 or 2 wherein said 2,2'-azoimidazole is a compound in which R is an alkyl group of 8 carbon atoms, $R^1$ and $R^2$ are hydrogen, n=2 and m=1.

8. The mesomorphic material of claims 1 or 2 in which said 2,2'-azoimidazole has two absorption bands in the visible part of the spectrum with their maximum at 430 and 550 mm., which have positive and negative dichroism respectively.

9. The mesomorphic material of claims 1 or 2 which comprises 1% of the compound of formula I and 99% of a mesomorphic matrix.

10. The mesomorphic material of claims 1 or 2 in which said matrix has a positive dielectric anisotropy.

* * * * *